United States Patent
Jansen

(10) Patent No.: US 9,726,151 B2
(45) Date of Patent: Aug. 8, 2017

(54) ASSESSMENT OF ROTOR BLADES

(75) Inventor: Gerhard Jansen, Vrees (DE)

(73) Assignee: WOBBEN PROPERTIES GmbH, Aurich (DE)

(*) Notice: Subject to any disclaimer, the term of this patent is extended or adjusted under 35 U.S.C. 154(b) by 144 days.

(21) Appl. No.: 14/116,236

(22) PCT Filed: Apr. 19, 2012

(86) PCT No.: PCT/EP2012/057188
§ 371 (c)(1),
(2), (4) Date: Mar. 3, 2014

(87) PCT Pub. No.: WO2012/152561
PCT Pub. Date: Nov. 15, 2012

(65) Prior Publication Data
US 2014/0161318 A1    Jun. 12, 2014

(30) Foreign Application Priority Data
May 11, 2011 (DE) .................. 10 2011 075 675

(51) Int. Cl.
| | |
|---|---|
| G06K 9/00 | (2006.01) |
| F03D 11/00 | (2006.01) |
| G01N 21/95 | (2006.01) |
| F03D 17/00 | (2016.01) |
| G06T 7/70 | (2017.01) |

(52) U.S. Cl.
CPC .......... *F03D 11/0091* (2013.01); *F03D 17/00* (2016.05); *G01N 21/9515* (2013.01); *G06T 7/70* (2017.01); *F05B 2270/804* (2013.01)

(58) Field of Classification Search
CPC ....... Y02E 10/721; Y02E 10/72; F03D 17/00; F03D 1/003; F03D 11/0091; F05B 2270/8041; G01C 15/00; G05D 1/0094; B43L 13/028; G01H 1/006; G01N 2291/2693
See application file for complete search history.

(56) References Cited

U.S. PATENT DOCUMENTS 3,254,414 A * 6/1966 Puthuff .................... G01B 3/08
                                                     33/771
2003/0095250 A1    5/2003   Kitagawa et al.
(Continued)

FOREIGN PATENT DOCUMENTS

DE          103 23 139 A1    12/2004
DE    10 2006 032 387 A1     1/2008
(Continued)

OTHER PUBLICATIONS

Peter Meinlschmidt, Jochen Aderhold. Thermographic Inspection of Rotor Blades. ECNDT 2006, 1-9.*

*Primary Examiner* — Bhavesh Mehta
*Assistant Examiner* — Ian Lemieux
(74) *Attorney, Agent, or Firm* — Seed Intellectual Property Law Group LLP

(57) ABSTRACT

The present invention concerns a method of optically assessing a wind power installation or a part thereof, in particular a rotor blade, including the steps: orienting a camera on to a region to be assessed, recording a photograph of the region to be assessed with the camera, detecting the position of the photographed region, and associating the ascertained position with the photographed region.

15 Claims, 3 Drawing Sheets

(56) References Cited

U.S. PATENT DOCUMENTS

| | | |
|---|---|---|
| 2004/0151578 A1 | 8/2004 | Wobben |
| 2008/0141778 A1 | 6/2008 | Bosselmann et al. |
| 2009/0266160 A1* | 10/2009 | Jeffrey .................... F03D 1/008 73/455 |
| 2010/0103260 A1* | 4/2010 | Williams ................ F03D 11/00 348/144 |
| 2010/0215212 A1 | 8/2010 | Flakes, Jr. |
| 2010/0277795 A1* | 11/2010 | Lopresti .............. G02B 23/165 359/430 |
| 2011/0138937 A1 | 6/2011 | Fritz |
| 2011/0206511 A1* | 8/2011 | Frydendal ............ F03D 7/0224 416/61 |
| 2012/0076345 A1* | 3/2012 | Fritz ...................... F03D 1/003 382/100 |
| 2013/0194567 A1* | 8/2013 | Wan ...................... G01B 11/14 356/152.1 |
| 2015/0043769 A1* | 2/2015 | Newman ................ G01N 25/72 382/100 |

FOREIGN PATENT DOCUMENTS

| | | |
|---|---|---|
| DE | 10 2008 053 928 A1 | 5/2010 |
| DE | 10 2009 009 272 A1 | 8/2010 |
| EP | 2 218 912 A2 | 8/2010 |
| JP | 4-87402 U | 7/1992 |
| JP | 5-322778 A | 12/1993 |
| JP | 2003-185589 A | 7/2003 |
| JP | 2010-229824 A | 10/2010 |
| JP | 2010-230595 A | 10/2010 |
| RU | 2162591 C1 | 1/2001 |
| SU | 135764 A1 | 11/1960 |
| TW | 401687 B | 8/2000 |
| WO | 2010/051278 A1 | 5/2010 |

* cited by examiner

ASSESSMENT OF ROTOR BLADES

BACKGROUND

Technical Field

The present invention concerns a method of assessing a wind power installation, in particular assessing rotor blades of a wind power installation, and a corresponding assessment apparatus.

Description of the Related Art

In particular the present invention concerns the assessment of a horizontal-axis wind power installation comprising a pylon and a pod with a rotor and rotor hub with a plurality of rotor blades, as is shown in FIG. 3.

Rotor blades of a wind power installation can nowadays be of lengths of up to 60 m and in that case are exposed to fluctuating wind loads and sometimes even storms. In that case considerable loadings occur on the rotor blade, and in particular on rotor blades which are made entirely or partly from a composite fiber material like for example glass fiber materials can be damaged in particular by such overloads. Such damage can be recognized for example by crack formations. It is important that such cracks or other indications of damage are recognized early in order to avoid major damage by the rotor blade being replaced or if possible repaired.

For that reason a regular inspection of rotor blades for any symptoms of damage can be appropriate. Such investigations are also referred to as assessments or appraisals. In principle such assessments can also be performed on other components of a wind power installation like for example the pylon or the pod. To perform rotor blade assessment, the procedure involved is frequently that the wind power installation is stopped and the surfaces of the rotor blades are inspected by means of equipment like cherry pickers, working platforms or abseiling devices. Such inspections are time-consuming and costly and the described operations at such heights also involve a risk for the service workers who perform those inspections, namely assessment operations, namely being a risk due to working at height.

As state of the art attention is directed at this juncture generally to the following documents: DE 10 2006 032 387 A1, DE 103 23 139 A1, DE 10 2008 053 928 A1, DE 10 2009 009 272 A1 and WO 2010/051 278 A1.

BRIEF SUMMARY

One embodiment of the invention is directed to an improved assessment of a wind power installation, in particular rotor blades thereof, with a less expensive way than previous solutions provided, and which reduces a working risk to service personnel who perform such an assessment.

According to one embodiment of the invention there is proposed a method that is adapted to optically assess a wind power installation or a part thereof, in particular a rotor blade or a plurality thereof, in succession, namely to optically inspect for any damage or first signs of damage or indications of damage. Accordingly a camera is used, which in particular may be a high-resolution digital camera. So-called webcams or special cameras are also considered. Preferably photographic cameras are proposed, but it is also possible to use film cameras. Such a camera is directed on to a region to be assessed, that is to say on to a region of the wind power installation, in particular a region of the rotor blade. A photograph is taken of that region with the camera. The photograph taken in that way can be evaluated on site or later and/or archived. On the basis of the photograph it is now possible to arrive at a visual finding in respect of the region to be assessed. In particular, such a photograph makes its possible to recognize cracking or to inspect the region to be assessed for cracking. Instead of a photograph it would also be possible to record a film sequence.

In relation to the region to be assessed or the assessed region, that is to say the photographed region, the position on the rotor blade is also detected, and associated with the photographed region and thus the respectively assessed region. To completely assess the rotor blade or the other region of the wind power installation the described procedure is to be repeated successively for all regions to be inspected of the respective part, that is to say for example the rotor blade. In that case, in relation to each assessed and thus photographed region, a respective position is detected and associated so that documentation of the assessment result for the rotor blade can also be provided.

Preferably the camera is equipped with a telescopic optical system, in particular a telescope, and for recording a photograph of the region to be assessed that region is optically magnified in order thereby to obtain a photograph of the highest possible resolution.

The use of a telescopic optical system, in particular in conjunction with a high-resolution digital camera, makes it possible to arrive at a high-quality optical assessment of the respective region from the ground so that it is possible to avoid working at height, that is to say working by means of lift platforms, platforms, abseiling devices or the like on the rotor blade or other regions of the wind power installation.

Preferably a rotor blade of a so-called horizontal-axis wind power installation which has a rotor blade root and a rotor blade tip is assessed. The rotor blade root is the part of the rotor blade which is fixed to the rotor hub and the rotor blade tip is the part of the rotor blade, that is remote from the hub.

In that case the rotor blade and the camera are preferably so oriented relative to each other that the same spacing is set between the camera and the rotor blade root on the one hand and the camera and the rotor blade tip on the other hand, or a longitudinal axis of the rotor blade, that is to say an axis from the rotor blade root to the rotor blade tip, is set perpendicularly to an optical axis, namely an optical axis which connects the camera to a central region of the rotor blade. If the camera is at a sufficiently great spacing relative to the rotor blade, which in most cases can already be the case when the camera is on the ground in the proximity of the wind power installation then in principle the spacing from the camera to each region of the rotor blade is approximately constant. Preferably however the camera at least is to be arranged on the ground on a camera stand to avoid working at a height as referred to above. Arranging the rotor blade in relation to the camera as stated can be effected for example in such a way that the wind power installation is shut down so that the rotor blade remains in a suitable selected position relative to the camera. Depending on the space on the ground in the region of the wind power installation the described orientation as between the rotor blade and the camera can also be implemented by suitable installation of the camera.

In a configuration it is proposed that a projection device having a projection surface is used to ascertain the position of the photographed region. That projection device is so adapted that a position corresponding to the assessed region is projected on to the projection surface, by virtue of the orientation of the camera. Here orientation of the camera is effected by the camera as such or at least a part thereof being moved for it to be directed on to the region to be assessed, and by it assuming a suitable oriented position after that orientation operation. That oriented position is projected on to the projection surface of the projection device.

Preferably a projection is effected by means of a lighting means on the camera. That lighting means can be for example a laser pointer or the like. In particular a light source involving minimum scatter should be used so that in relation to each orientation of the camera, a light dot or at least a light spot on the projection surface specifies a position corresponding to the respective region which is assessed or is to be assessed.

In other words the projection device is so adapted that, upon continuous scanning of a silhouette of the rotor blade—this is described here only for illustration purposes—this gives an in particular reduced-size image on the projection surface if the corresponding movement of the light dot or spot of the lighting means were traced. A rigid connection between the lighting means and the camera to be oriented provides that each orientation can be easily drawn on the projection surface and documented. The projection surface can be for example a drawing sheet of a flipchart and each position is then drawn by hand on that flipchart corresponding to the respectively occurring light dot or light spot. Likewise a measurement recording device which detects the respective position in an automated procedure can be provided as the projection surface. With automated detection determining the orientation of the camera in a different way is also envisaged, like for example by a rotary rate sensor. The preferred use of a projection surface which is to be written upon manually is however simple, inexpensive and advantageous.

To be able to associate the positions of the assessed regions, which positions are respectively recorded on the projection surface, with positions on the rotor blade, the rotor blade can be plotted for example in its silhouette or in some corner points on a reduced scale on the projection surface. In particular the position of the rotor blade tip and the root region, in particular specifically the flange for fixing to the rotor blade, are considered as being recorded for that purpose for orientation purposes. For that purpose the camera can be oriented in relation to the rotor blade tip and then the flange of the rotor blade, in which case the respective corresponding point is plotted on the projection surface. On the basis at least of those two corner points, scaling is then possible by way of the knowledge of the rotor blade dimensions, in particular the blade length.

It is preferably proposed that rotor blade scaling be provided on an elastic band like a rubber band. When therefore a scaling of the known rotor blade is recorded on the rotor blade, the elastic band only needs to be stretched in such a way that it joins the point which has just been plotted of the rotor blade tip to the plotted point of the flange of the rotor blade. In that case scaling on the elastic band is uniformly stretched and then only still needs to be transferred on to the projection surface. Likewise—if this is necessary—scaling can also be implemented in the transverse direction of the rotor blade.

According to one embodiment of the invention there is also provided an assessment apparatus that is adapted to visually assess a rotor blade of a wind power installation. In principle assessment of other components like the pylon or the pod of the wind power installation is also envisaged herewith.

The assessment apparatus has a camera for recording a respective photograph of a region of the rotor blade, that is to be assessed. Connected to the camera is an orientation apparatus for orienting the camera on to the region to be assessed. In particular an adjustable stand, that is to say a stand with an arrestable or lockable motion mechanism for the camera can be used for that purpose. The assessment apparatus further has a position detection device adapted to detect the respective position of the region to be assessed or the assessed region.

Preferably the camera is provided with a telescopic optical system, in particular a telescope, to optically magnify the regions to be assessed, in particular to be able to record a magnified photograph of the respective region to be assessed. Preferably a high-resolution photographic camera is used in particular together with such a telescopic optical system.

In an embodiment the position detection device is in the form of a projection device having a projection surface. Preferably the camera is connected to a lighting means, in particular a laser pointer to produce a light spot on the projection surface at a position corresponding to the position of the region to be assessed on the rotor blade.

A further embodiment proposes the provision of a data processing device for associating the respective photograph of the respective region to be assessed with the detected position of the region to be assessed. Preferably that data processing device is adapted to store a photograph with the associated position. That proposes a higher degree of automation which permits optical assessment of a rotor blade with subsequent documentation, wherein the documentation can be taken over entirely or partially by the data detection device. That saves time and avoids sources of error.

It is desirable if the orientation device has at least one electronic control and a motor drive for automated orientation of the camera. That can provide for optical assessment in a simple fashion. It is possible in that way for the regions of a rotor blade, that are to be assessed, that is to say in particular all the surface regions of a rotor blade, to be successively scanned, for a respective photograph or, to be on the safe side, a plurality of photographs, to be taken for each region, for it to be documented and archived. Even if no crack or other initial sign of rotor blade damage were found, such documentation can serve as later proof, such as for comparison to later obtained photographs. The assessment of the rotor blade or another part of a wind power installation, by the assessment apparatus, more specifically in particular from the ground, makes it possible to provide suitable automation technology for the assessment apparatus.

Preferably such an automated orientation device is coupled to the data processing device to be controlled by the data processing device. In that way implementation and archiving of the assessment and possible also evaluations of the assessment can be implemented in automated fashion. As a result corresponding time savings and improved levels of reproducibility are to be specified as advantages here. Preferably the data processing device has image processing software which can evaluate or at least subject to preliminary evaluation each image for cracking or other known initial signs of damage.

Finally, for enhanced automation and the avoidance of complicated and expensive operations at a height, a safety aspect is also to be named as a further advantage here. More specifically, if a very great simplification in assessment can be achieved, then an assessment can also be readily performed at shorter intervals, thereby guaranteeing a higher level of safety. If an automated assessment of the rotor blade is effected then markedly shorter stoppage times of the wind power installation are also necessary during the assessment procedure.

Thus there is proposed a method of and an apparatus for optical assessment of parts of a wind power installation, in particular regions of a rotor blade. That aims to achieve in particular savings in respect of cost and time in the assessment of rotor blades, as well as minimizing risks due to working at a height. In addition, it is possible to achieve optimization of operational planning for a rotor blade service, that is to say the service which rotor blade assessments usually involve. In addition a mass assessment is possible or at least is made easier, and an improvement in operational planning of rotor blade maintenance operations can be effected for example in such a way that the assessment is effected at the right moment in time on the right installation. In addition this promotes condition-oriented maintenance. A fast assessment in respect of rotor blades and thus short stoppage times also enhances the acceptance on the part of the wind power installation operator for accepting such an assessment and a stoppage linked thereto.

The proposed assessment and assessment apparatus aims in particular at an assessment from the ground. In principle a commercially available telescope can be used, which is suitable for terrestrial observations. Such modern telescopes have the advantages that they are inexpensive, transportable and in part finely controllable, namely both manually and also by way of a computer. Further advantages are that known camera technology can be adopted, such as for example a webcam or high-grade camera technology. In principle the use of special cameras for thermal images or infrared recordings is also considered. Preferably a high-resolution camera should be used, which however can be limited in combination with a telescope. It is also possible to use software for processing and control. For special applications such as for example specific adaptation to the shape of the rotor blade to be assessed, systems used can permit open interfaces for adaptations to specific applications.

A possible way of implementing assessment is effected by a telescope under the mark "Meade", type designation LX90, as for example on the Internet page http://www.meade.com/lx90/index.html. This involves an 8 inch device which has GPS and a compass and is oriented by motor means.

The orientation of that telescope is substantially automatically effected for astronomical observations by means of GPS and compass. In the terrestrial mode which can be used for the assessment procedure the telescope is preferably positioned and controlled manually by way of a remote operating system. Here too however adaptation can preferably be effected by way of provided interfaces and automation can be provided for recurrent checking operations.

In principle purely manual assessment by means of a telescope, that is to say exclusively by viewing through the telescope, can be performed. In principle however, for photograph documentation, it is proposed that a high-grade 20 Megapixel camera of type Canon EOS5D or a commercially available webcam like for example Logitech 2 Megapixel camera or a commercially available small digital camera like for example a Canon Powershot A460, 5 Megapixel, is used. Other cameras can also be used and adapted to a suitable telescope such as for example a camera from the corporation "The Imaging Source".

Instead of the above-mentioned 8 inch device the use of a 10 inch or 12 inch device is proposed.

The structure of an assessment apparatus as well as orientation and direction of the rotor blade is described hereinafter by means of a specific example.

A telescope is used, mounted on a stable stand. As an embodiment, it is proposed that the equipment, that is to say in particular the telescope, is to be provided on a vehicle, in which the telescope can remain completely on the vehicle. For that purpose, a frame is used for the vehicle and can be let down through a vehicle floor. In that case the telescope stands on the frame which can be let down so that the telescope then has a firm stand on the ground, and is nonetheless in the vehicle, and is at least partially disposed in the vehicle. That makes it possible to reduce equipment setup times involved in setting up and taking down the telescope. In principle it is possible to drive with the vehicle to the desired location, to open the corresponding vehicle door and to start the assessment procedure. Letting down the frame through the vehicle floor provides that the vehicle and the telescope are uncoupled from each other. In that way the quality of the images can be crucially improved or it is first possible in that way to achieve high quality because in particular a more stable setup should be guaranteed for that purpose. Alternatively or additionally it is possible to use stabilizing systems for stabilizing the image, and this is proposed as an embodiment. For orientation purposes the telescope can be controlled under computer control or manually by way of a remote control. A camera can be fitted over the eyepiece of the telescope.

The rotor blade is so positioned that an almost identical spacing between the rotor blade and telescope or camera is achieved over the length of the blade. Range measurement can be effected for example with a so-called range finder.

In that case, firstly the distance between the telescope and the blade enlargement or underside of the pod is determined. That spacing must then also be set between rotor blade tip, that is to say the tip, and the telescope. For that purpose the rotor can initially idle, that is to say basically be rotated by the wind but without force, in order then to stop the rotor at the correct moment at the control cabinet of the wind power installation by actuation of the emergency off switch and thus to stop the rotor blade to be inspected at the desired location.

A spacing as constant as possible between the telescope and rotor blade or another component to be inspected, over the entire rotor blade length or component length, provides that little or no re-focusing at all has to be effected. Focusing for assessment of the entire rotor blade can possibly be sufficient. If the rotor blade is not oriented in that desired fashion optical assessment can nonetheless be carried out, but leads to a higher degree of focusing involvement.

For orientation to the rotor blade, mounted on the telescope or the camera is a laser pointer which projects a dot on a flipchart behind the telescope. For orientation on the rotor blade, the tip is approached with the telescope and the tip position marked on the flipchart. In the case of an Enercon E82 wind power installation that corresponds to a radius 41 m. Next the root region or the blade skirt is approached, this basically also being the same as a flange of the rotor blade for fixing it to the rotor hub. For the example of the Enercon E82 wind power installation that corresponds to a radius of 3.1 m. That dot is also marked on the flipchart and the other radii between those two points can be easily determined.

Radii, for example at the spacing of meters, are either calculated and identified on the flipchart or an elastic band, in particular a rubber band, is used, on which a raster pattern for the wind power installation, that is to say in the above example for the rotor blade of the Enercon E82 wind power installation, is identified. The spacing between the telescope and the rotor blade can vary from one installation to another and the spacing between the telescope and the flipchart, that is to say the projection surface, can also slightly vary. By stretching the elastic band and therewith the rubber band raster pattern shown thereon, the reference dimensions can be easily transferred on to the flipchart. Alternatively for example a reference dimension, that is to say a scaling by means of an inch rule, can be provided on the flipchart, that is to say drawn thereon, and the associated radii can be calculated. In addition there is the possibility of implementing orientation by way of angle information or angle details of the telescope, and the geometrical conditions involved. It is preferably proposed that reference marks be provided on the rotor blade, which a suitable system like a data processing device which is connected to the assessment apparatus, in particular the camera, reads in and processes. That makes it possible to effect or improve orientation in relation to the rotor blade.

In an embodiment of the invention there is proposed a method which is characterized in that, to detect the position of the photographed region, at least one orientation angle of the camera or a telescopic optical system used is detected in relation to a reference orientation. The position of the respectively photographed and thus assessed region can be determined by the detection of such an angle. For that purpose, the angle can be detected in one direction, for example a longitudinal direction of the assessed part, to detect a position in respect of that direction on the part. Optionally at least one further angle can additionally be recorded in particular in a transverse direction relative to the stated longitudinal direction or transversely relative to another first direction in order to be able to determine an assessed region in two directions in order thereby to determine a respective position on a surface, that is to say in two-dimensional mode. The underlying options are described hereinafter in particular for detecting an angle in a direction, which however can also be appropriately readily applied to the use of at least two angles.

An actual location on the part to be assessed, in the sense of coordinates or dimensions, can be associated by way of known relationships, from a recorded angle. In other words, angle values can be converted by calculation into corresponding length values. Alternatively the angle values can simply be stored as reference values without calculation conversion. The orientation angle relates to a reference orientation which can be arbitrarily fixed. A possible way of establishing the reference orientation is to associate therewith a characteristic point on the part to be assessed, such as for example in the middle or at the edge of the part to be assessed.

It is preferably proposed that at least one dimension be detected in a longitudinal direction of the part to be assessed, from a first reference point to a second reference point on that part. For example the part to be assessed can be a rotor blade and the first reference point is at the root of the rotor blade and the second reference point is at the rotor blade tip. Detection of the dimensions in the longitudinal direction, that is to say in this example detection of the length of the rotor blade, can also be effected by the corresponding value already being known or by it being taken from a data sheet.

In addition a first reference angle and a second reference angle are recorded. The reference angles respectively relate to the orientation angle of the camera or telescopic optical system in relation to the first and second reference points respectively. In the specified example the first reference angle thus given the angle upon orientation in relation to the rotor blade root and the second reference angle gives the orientation angle upon orientation in relation to the rotor blade tip. In that way, a differential angle between the first and second orientation angles is also known or can be easily calculated. In addition the dimension, that is to say the rotor blade length in the specified example, can be associated with such a differential angle.

In addition, a respective currently prevailing orientation angle of the camera or telescopic optical system in relation to the currently assessed region is recorded. The current orientation angle is thus that angle which is set when the photographic camera or the telescopic optical system is directed towards the respective region to be assessed. That current orientation angle can be associated with the photograph, which is recorded in that case, of the respective region. Preferably it is stored together with the photograph or with an identification code such as a reference number of the recorded photograph, in a table.

Alternatively or additionally the current position can be determined from the currently prevailing orientation angle, having regard to the two reference angles and the dimension. That can be effected for example by interpolation.

If for example a 50 m long rotor blade is oriented for the assessment operation perpendicularly to a viewing direction from an assessment apparatus and if the first reference angle, that is to say the angle relative to the rotor blade root, is 5 degrees and the second reference angle, namely the angle relative to the rotor blade tip, is −5 degrees, then in a first approximation a dimension of 5 m is to be associated with each degree. If therefore a current orientation angle is for example 2 degrees, then the associated assessed region is 15 m below the rotor blade root. That position can be stored in a table together with a reference number for the photograph of that region. Even smaller angle steps can be associated with a position. The association can be implemented for example by interpolation. Alternatively, the position can be even more accurately calculated using trigonometric functions and stored or alternatively can first be stored and later calculated.

Preferably an assessment apparatus thus has a position detection device including an angle detection means. That angle detection means can detect an orientation angle of a camera, in particular a photographic camera, and/or a telescopic optical system, and in particular subject it to further processing by data processing technology, such as for example being transferred to a connected data processing device. The angle detection means can be a compass and/or a rotary rate sensor and/or a bubble level in order thereby to be able to determine a relative and/or an absolute angle. Further technical implementations are also possible.

The use of a position detection device by means of an angle detection means can be effected alternatively or additionally to the detection of an assessed position by means of a projection device.

BRIEF DESCRIPTION OF THE SEVERAL VIEWS OF THE DRAWINGS

The invention is described by way of example hereinafter by means of embodiments with reference to the accompanying Figures.

DETAILED DESCRIPTION

Figure 1:
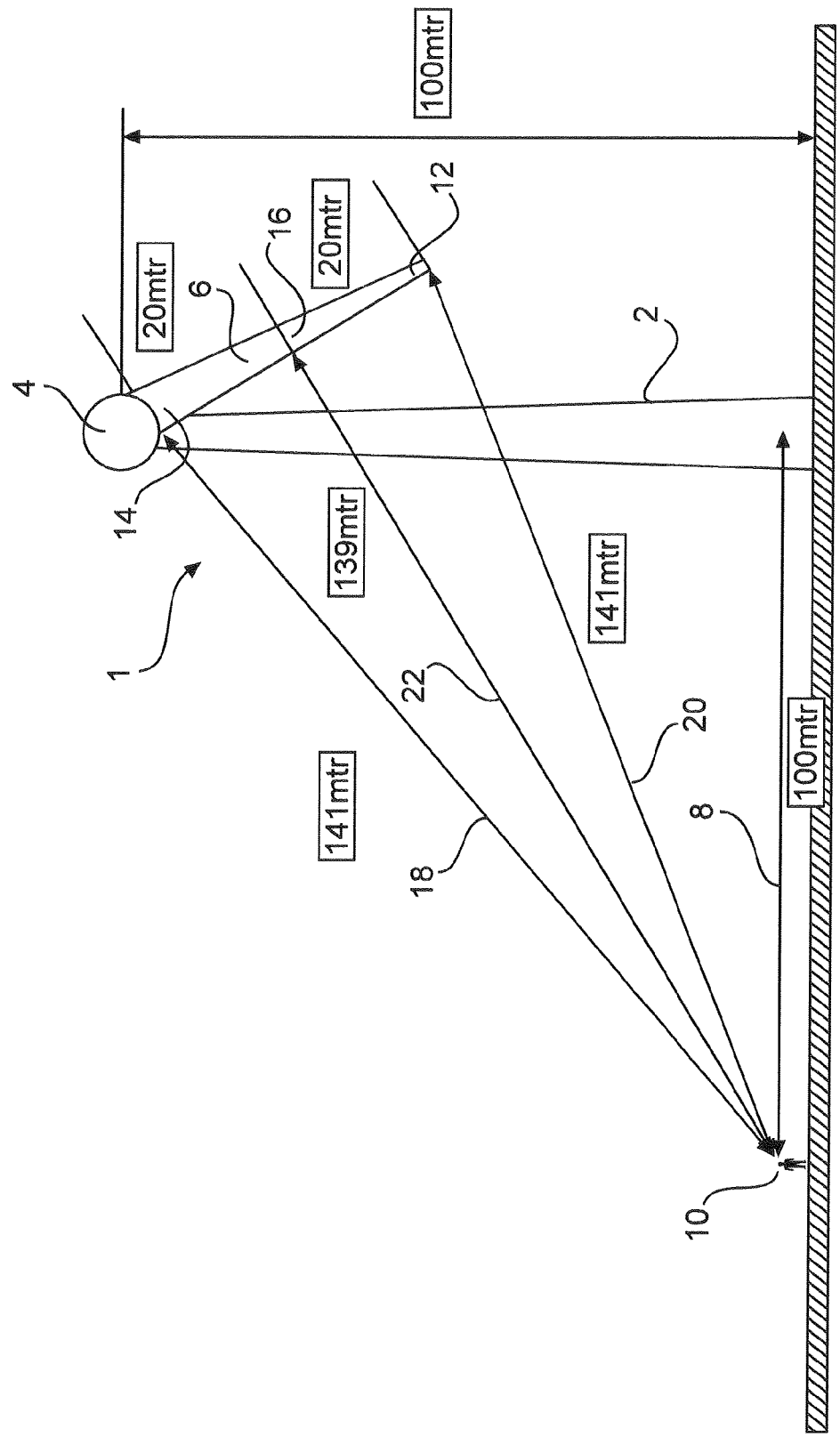
FIG. 1 diagrammatically shows an arrangement with a wind power installation readied for assessment, FIG. 2 diagrammatically shows a rotor blade assessment apparatus, and FIG. 3 diagrammatically shows a wind power installation.

FIG. 1 diagrammatically shows a wind power installation 1 comprising a pylon 2 and a pod 4 or hub 4 which has three rotor blades 6 of which only one is shown in FIG. 1.

An observer 10 is at an observation distance 8 from the pylon 2. The observation distance 8 is indicated by a double-headed arrow and in the present example is 100 m, which only represents a value by way of example.

Here assessment is to be effected from the position of the observer 10.

The rotor blade 6 has a rotor blade tip 12 which here is also referred to simply as the "tip". Towards the pod or hub 4 the rotor blade 6 has a root region 14 with a flange for fixing to the pod or hub 4. In this respect the flange is not shown in detail but basically forms the contact region of the hub with the rotor blade 6. A central region 16 is located between the rotor blade tip 12 and the root region 14.

For the assessment operation, the wind power installation is stopped in such a way that the rotor blade 6 to be inspected comes to a stop. In one embodiment the location at which the rotor blade is stopped is such that the spacing between the root region 14 and the rotor blade tip 12 relative to the observer 10 is substantially equal. If the observation distance 8 and thus the distance of the observer 10 from the rotor blade 6 is only sufficiently great, the distance from the observer 10 to the central region 16 of the rotor blade 6 also approximately corresponds to the distance from the observer 10 to the root region 14 and the rotor blade tip 12 respectively of the rotor blade 6.

Figure 2:
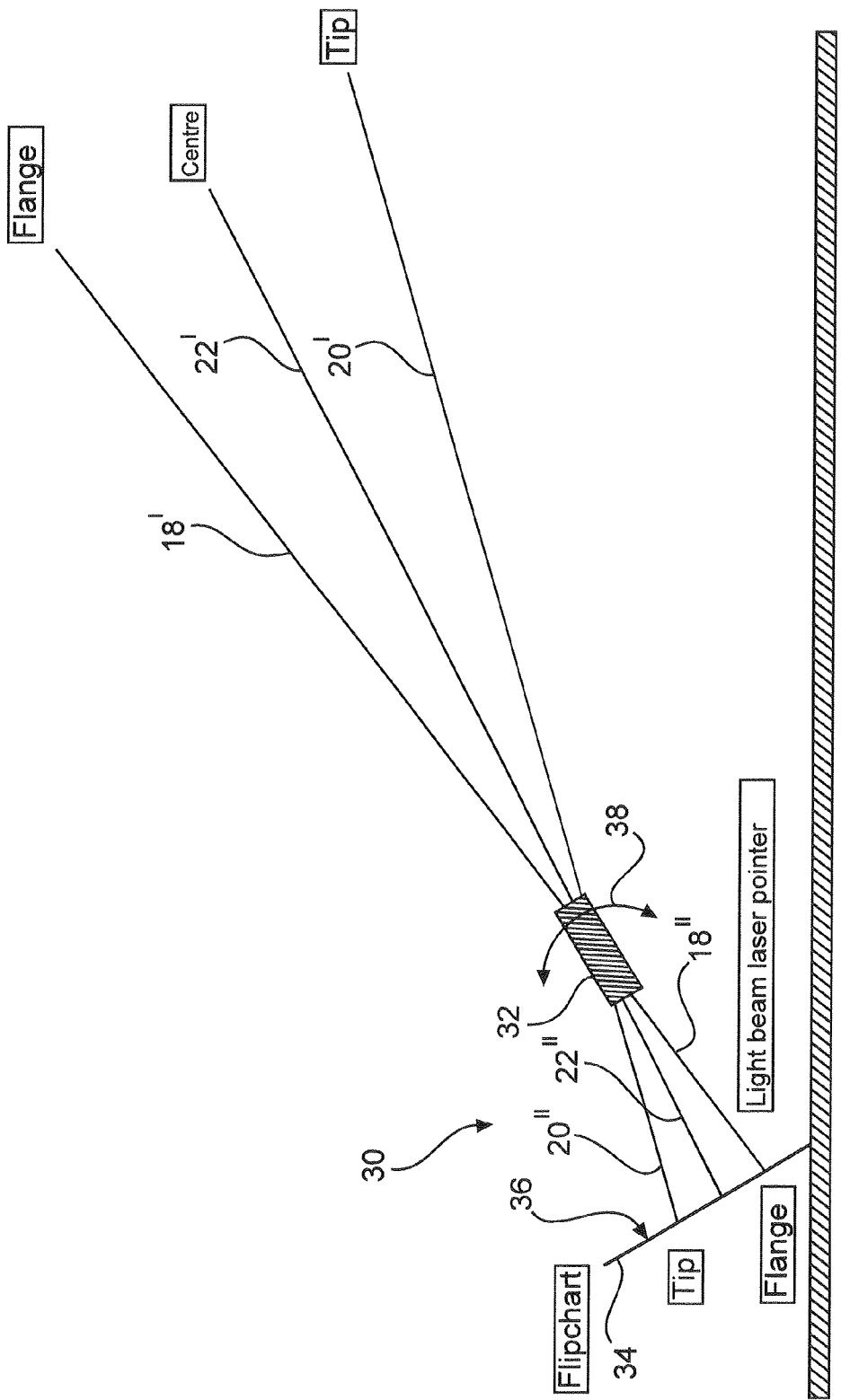
Figure 3:
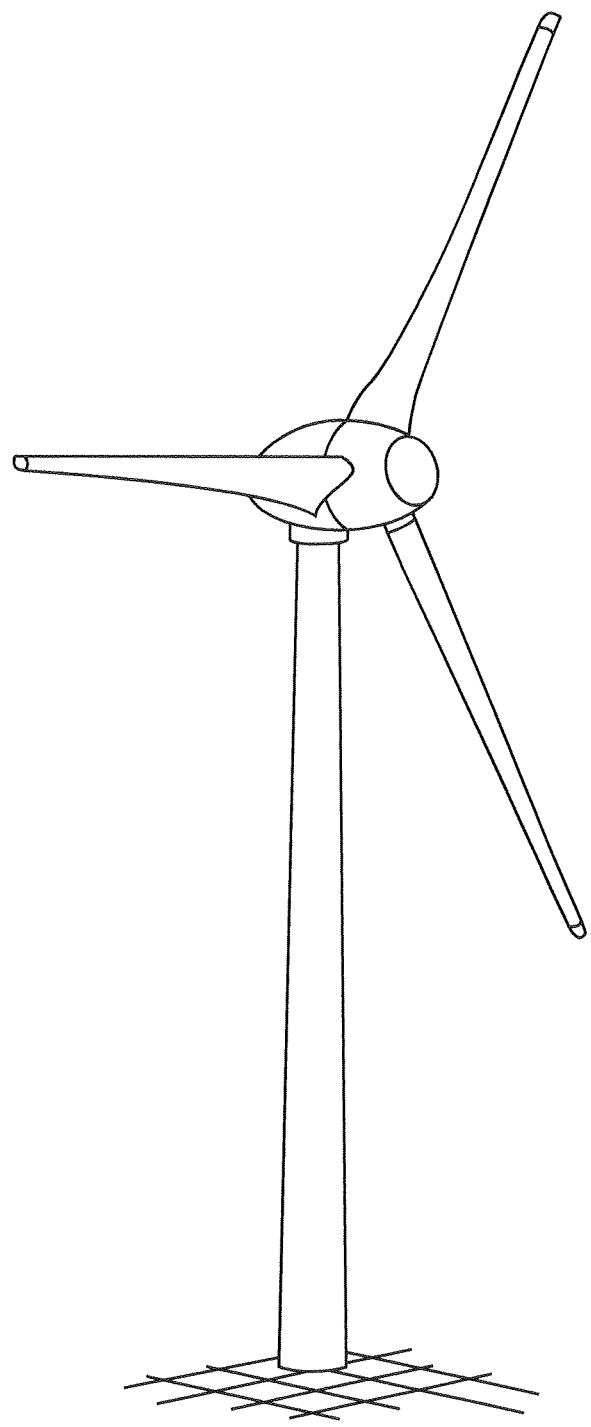

In the example selected in FIG. 2 for illustration purposes the wind power installation 1 has a hub height of 100 m. The observation distance 8 from the observer 10 to the pylon 2, namely to the pylon base, is also 100 m. There is however no need for the observation distance 8 to correspond to the hub height. That preferred configuration however is well suited for describing the present assessment method. The length of the rotor blade 6 in the illustrated example is 40 m wherein for the sake of simplicity the center point of the rotor hub 4 is assumed to be the same as the root region 14 of the rotor blade 6. The flange distance 18, that is to say the distance from the observer 10 to the root region or flange region 14 of the rotor blade 6, is thus 141 m.

The rotor has now been stopped in such a position that the rotor blade 6 is in such a position that the tip distance 20, namely the distance from the observer 10 to the rotor blade tip, is the same as the flange distance, namely 141 m. The tip distance can also be referred to as the distance in relation to the rotor blade tip. Accordingly there is a central region distance 22, namely the distance of the observer 10 relative to the central region 16 of the rotor blade 6, which is 139 m. Accordingly this involves approximately—to a few meters—an identical distance from the observer 10 to different regions of the rotor blade 6. Thus for observation of the rotor blade from the observer 10 by means of an optical device, one-off focusing may be sufficient for assessment of the entire rotor blade 6. For that purpose, in the illustrated example, the depth of focus or correction of the depth of focus or sharpness of the optical device only needs to be or compensate for about 2 m.

An assessment arrangement 30, that is to say an arrangement for carrying out an assessment of a rotor blade, is shown in FIG. 2. The assessment arrangement 30 includes a camera 32, in particular a digital photographic camera, as well as a projection recording means 34 having a projection surface 36. By way of example the projection recording means used can be a so-called flipchart, that is to say a board with writing or drawing paper. The camera 32 is preferably fixed on a support stand—not shown in the diagrammatic view in FIG. 2—with the stand oriented in a direction towards the rotor blade 6, towards the respective region thereof that is to be assessed. The camera 32 is thus oriented successively on to surface regions of the rotor blade 6 to be assessed and the corresponding regions are photographed and can be evaluated on site or subsequently at a different location. FIG. 2 shows by way of example the orientation 18' towards the flange or root region 14 of the rotor blade 6, the orientation 20' in the direction towards the tip or rotor blade tip 12, and the orientation 22' towards the central region 16 of the rotor blade 6. The orientations 18', 20' and 22' thus extend along the lines shown in FIG. 2 which illustrate the flange distance 18, the tip distance 20 and the central region distance 22 respectively.

For the sake of completeness it should be mentioned that FIGS. 1 and 2 illustrate the assessment method by way of example in one plane, and accordingly the orientation of the camera 32 only alters along a longitudinal axis of the rotor blade 6. It will be appreciated that in actual fact an orientation transversely relative to the longitudinal axis of the rotor blade can also be altered. FIG. 2 shows, for orientation purposes, a pivotal direction 38 with a corresponding double-headed arrow, by which the camera 32 can be oriented along the longitudinal direction of the rotor blade, whereas a second pivotal direction for orientation transversely relative to the longitudinal direction of the rotor blade 6 extends into the plane of the drawing in FIG. 2 and is not shown for that reason.

The camera 32 also has a lighting means such as for example a laser pointer or modified laser pointer which produces a light beam along the optical axis of the camera 32 in the rearward direction, namely from the camera 32 towards the projection surface 36. For the orientations shown in FIG. 2, namely the orientation 18' towards the flange, 20' towards the tip and 22' towards the central region, corresponding projection beams are shown, corresponding to the corresponding orientation. Thus there is a flange projection beam 18" in relation to a flange orientation 18', a tip projection beam 20" in relation to the orientation 20' to the tip and a central region projection beam 22" in relation to the central region orientation 22'. Assessment of the rotor blade 6 can be documented on the projection surface 36 by way of the resulting light spot on the projection surface 36. Thus for example for each photograph which is taken in a region of the rotor blade 6, a corresponding data file number, for example a number of the photographic data file, can be noted at the corresponding position on the projection surface 36.

That rearwardly emitted light beam, which can also be provided in other directions, provides that the entire shape, for example a silhouette of the rotor blade, can be drawn on the projection surface 36, which for example can be a sheet of drawing paper. The rotor blade projected in that way is rotated through 180 degrees with respect to the original rotor blade 6 and reduced in scale. As the size of the rotor blade to be assessed is known scaling of the projection on the projection surface 36 is easily possible. For example, for the sake of simplicity, it is also possible to provide a scaling which is to be expected or a scaling recorded in an earlier assessment of a wind power installation of the same structure, on a rubber band. In that way the scaling can be easily transferred to the new projection by the rubber band carrying the scaling being stretched to the new size, in the event of slight deviations in the size relationships. The scaling is proportionately adapted and does not need to be freshly calculated in detail.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet, including but not limited to [insert list], are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of optically assessing a portion of a wind power installation, the method comprising:
    placing a camera at a distance in front of the rotor of the wind power installation;
    successively orienting a camera toward surface regions of the rotor blade to be assessed;
    using the camera, recording photographs of the surface regions to be assessed;
    using a position detection device, determining the positions of the photographed surface regions, wherein determining the positions of the photographed surface regions comprises:
        detecting at least one dimension in a longitudinal direction of the surface regions to be assessed from a first reference point to a second reference point of the surface regions,
        recording at least one first reference angle that specifies a first orientation angle relative to the first reference point,
        recording at least one second reference angle that specifies a second orientation angle relative to the second reference point,
        recording a current orientation angle that specifies an orientation angle relative to the surface regions to be assessed, and
        determining a current position of the surface regions to be assessed in relation to the longitudinal direction of the surface regions, the current orientation angle, and the reference angles;
    associating the determined positions with the recorded photographs;
    using the recorded photographs to identify a crack in the rotor blade at the determined positions; and
    correlating the crack with a location on the rotor blade.

2. The method according to claim 1 wherein a camera with a telescopic optical system is used to record the photographs and the surface regions to be assessed is optically magnified for recording photographs using the telescopic optical system.

3. The method according to claim 1 wherein the portion of the wind power installation being optically assessed is a rotor blade having a rotor blade root and a rotor blade tip, and the rotor blade and the camera are oriented relative to each other so that a distance between the camera and the rotor blade root is substantially the same as a distance between the camera and the rotor blade tip.

4. The method according to claim 2 wherein determining the positions of the photographed surface regions comprises determining at least one of an orientation angle of the camera and the telescopic optical system in relation to a reference orientation.

5. The method according to claim 1 wherein the portion of the wind power installation is a rotor blade and the first reference point is in a root region of the rotor blade and the second reference point is at a tip of the rotor blade.

6. The method according to claim 1 wherein placing the camera at a distance in front of the rotor of the wind power installation comprises orientating a camera a distance from a rotor blade such that a tip of the rotor blade and a flange of the rotor blade are substantially the same distance from the camera.

7. A method of optically assessing a portion of a wind power installation, the method comprising:
    placing a camera at a distance in front of the rotor of the wind power installation;
    successively orienting a camera toward surface regions of the rotor blade to be assessed;
    recording photographs of the surface regions to be assessed;
    determining the positions of the photographed surface regions, wherein determining the positions of the photographed surface regions comprises using a projection device having a projection surface for projecting a position corresponding to the surface regions to be assessed on to the projection surface by the orientation of the camera; and
    associating the determined positions with the recorded photographs.

8. The method according to claim 7 wherein the camera has a lighting means for emitting light on to the projection surface in dependence on the orientation of the camera so that a light spot is visible on the projection surface.

9. The method according to claim 8 wherein the projection surface is scaled by means of a scaling plotted on an elastic band, wherein the elastic band is stretched for scaling of the projection surface to a distance to be scaled.

10. An assessment apparatus for optical assessment of a rotor blade of a wind power installation, the assessment apparatus comprising:
    a camera configured to record a photograph of a region to be assessed of the rotor blade;
    an orientation device connected to the camera configured to orient the camera toward the region to be assessed, wherein the orientation device has at least an electronic control and a motor drive for automated orientation of the camera; and
    a position detection device configured to detect a position of the region to be assessed by:
    detecting at least one dimension in a longitudinal direction of the region to be assessed from a first reference point to a second reference point of the region,
    recording at least one first reference angle that specifies a first orientation angle relative to the first reference point,
    recording at least one second reference angle that specifies a second orientation angle relative to the second reference point,
    recording a current orientation angle that specifies an orientation angle relative to the region, and
    recording a current position of the region in relation to the longitudinal direction of the surface regions, the current orientation angle, and the reference angles,
    wherein the position detection device, upon detecting a position of the region to be assessed enables using the recorded photographs for identifying a crack in the rotor blade at the detected position of the region and correlating the crack with a location on the rotor blade.

11. The assessment apparatus according to claim 10 wherein the camera includes a telescopic optical system configured to optically magnify the region to be assessed prior to recording the photograph.

12. The assessment apparatus according to claim 10 wherein the position detection device is a projection device having a projection surface and includes a laser pointer configured to illuminate the projection surface at a position corresponding to the position of the region to be assessed.

13. The assessment apparatus according to claim 12 further comprising a data processing device configured to associate the photograph of the region to be assessed with the detected position of the region to be assessed and storing the photograph with the associated position.

14. The assessment apparatus according to claim 13 wherein the data processing device has image processing software configured to evaluate the recorded photograph of the region to be assessed.

15. The assessment apparatus according to claim 10 wherein the position detection device includes an angle detection means configured to record at least one orientation angle of the camera and a telescopic optical system.

\* \* \* \* \*